(12) United States Patent
Sachs et al.

(10) Patent No.: US 9,801,618 B2
(45) Date of Patent: Oct. 31, 2017

(54) LAPAROSCOPIC SURGICAL SCAFFOLD

(71) Applicant: Vicarious Surgical Inc., Cambridge, MA (US)

(72) Inventors: Adam David Sachs, Cambridge, MA (US); Sammy Mohsen Khalifa, Cambridge, MA (US); Barry Stuart Greene, Rockville, MD (US)

(73) Assignee: Vicarious Surgical Inc., Cambridge, MA (US)

( * ) Notice: Subject to any disclaimer, the term of this patent is extended or adjusted under 35 U.S.C. 154(b) by 1128 days.

(21) Appl. No.: 13/940,658

(22) Filed: Jul. 12, 2013

(65) Prior Publication Data

US 2014/0018684 A1 Jan. 16, 2014

Related U.S. Application Data

(60) Provisional application No. 61/671,140, filed on Jul. 13, 2012.

(51) Int. Cl.

| A61B 17/02 | (2006.01) |
|---|---|
| A61B 1/06 | (2006.01) |
| A61B 5/00 | (2006.01) |
| A61B 1/32 | (2006.01) |
| A61B 1/00 | (2006.01) |
| A61B 1/313 | (2006.01) |
| A61B 90/30 | (2016.01) |
| A61B 90/50 | (2016.01) |
| A61B 17/00 | (2006.01) |

(52) U.S. Cl.
CPC ...... *A61B 17/0218* (2013.01); *A61B 1/00124* (2013.01); *A61B 1/0684* (2013.01); *A61B 1/3132* (2013.01); *A61B 1/32* (2013.01); *A61B 5/0084* (2013.01); *A61B 17/0281* (2013.01); *A61B 90/30* (2016.02); *A61B 90/50* (2016.02); *A61B 2017/00283* (2013.01); *A61B 2017/00477* (2013.01)

(58) Field of Classification Search
CPC ... A61B 90/35; A61B 90/50; A61B 2090/506; A61B 2090/571; A61B 5/6835; A61B 17/0206; A61B 6/0471
USPC ................. 600/222, 229, 233, 234
See application file for complete search history.

(56) References Cited

U.S. PATENT DOCUMENTS

| 2,053,868 A | 9/1936 | Grosso |
|---|---|---|
| 2,313,164 A | 3/1943 | Nelson |

(Continued)

FOREIGN PATENT DOCUMENTS

WO WO-2014011969 1/2014

OTHER PUBLICATIONS

"International Application Serial No. PCT/US2013/050235, PCT Search Report and Written Opinion dated Nov. 1, 2013", 7 pages.

(Continued)

*Primary Examiner* — Anu Ramana
(74) *Attorney, Agent, or Firm* — Strategic Patents, P.C.

(57) ABSTRACT

A collapsible scaffolding can collapse for deployment to a laparoscopic surgical site through a trocar or the like, and can expand to provide a surface for organ retraction within a body cavity. In the expanded state, the scaffolding may assist a surgical procedure in a variety of ways, such as by providing a rigid structure upon which to secure retracted organs or surgical tools such as lights, cameras, and so forth.

21 Claims, 8 Drawing Sheets

(56) References Cited

U.S. PATENT DOCUMENTS

| | | | |
|---|---|---|---|
| 4,573,452 A | | 3/1986 | Greenberg |
| 5,755,661 A | | 5/1998 | Schwartzman |
| 6,162,172 A | * | 12/2000 | Cosgrove ........... A61B 17/0293 |
| | | | 600/208 |
| 7,691,058 B2 | * | 4/2010 | Rioux ................ A61B 17/0293 |
| | | | 600/231 |
| 2006/0052669 A1 | * | 3/2006 | Hart ........................ A61B 1/32 |
| | | | 600/206 |
| 2012/0046525 A1 | * | 2/2012 | Russell .............. A61B 17/0218 |
| | | | 600/204 |

OTHER PUBLICATIONS

WIPO, "International Application Serial No. PCT/US13/050235, Preliminary Report on Patenability dated Jan. 22, 2015", 6 pages.

\* cited by examiner

LAPAROSCOPIC SURGICAL SCAFFOLD

CROSS-REFERENCE TO RELATED APPLICATIONS

This application claims the benefit of U.S. Provisional App. 61/671,140, filed Jul. 13, 2012, the entirety of which is incorporated herein by reference.

BACKGROUND

Laparoscopic surgery involves creating one or more relatively small incisions in a subject that provide a surgeon's tools with access to a surgical site. Laparoscopic surgery enjoys certain advantages over more invasive procedures because the small surgical incisions often require less time to heal, are less painful, and leave smaller scars. On the other hand, in these minimally invasive techniques a surgeon generally operates in a highly constrained space within a patient's body such as the abdominal cavity.

Moreover, inside the abdominal cavity, organs and other tissue may obstruct access to a surgical site. For example, with a patient lying supine on an operating table, the patient's liver typically covers the gallbladder. Thus, laparoscopic procedures on a gallbladder often involve a precursor step of moving and securing the patient's liver away from the surgical site. This typically requires an additional person to manipulate the liver during the procedure and perform related tasks such as manipulating a light or camera, which can further limit the surgeon's working space inside and outside the abdominal cavity.

There remains a need for improved surgical tools to simplify laparoscopic surgical procedures.

SUMMARY

A collapsible scaffolding can collapse for deployment to a laparoscopic surgical site through a trocar or the like, and can expand to provide a surface for organ retraction within a body cavity. In the expanded state, the scaffolding may assist a surgical procedure in a variety of ways, such as by providing a surface to manually expand the cavity, or by providing a rigid structure upon which to secure retracted organs or surgical tools such as lights, cameras, and so forth.

BRIEF DESCRIPTION OF THE FIGURES

The invention and the following detailed description of certain embodiments thereof may be understood by reference to the following figures.

DETAILED DESCRIPTION

In the following description, references to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus the term "or" should generally be understood to mean "and/or" and so forth.

Terms of degree, such as "about" or "substantially" are intended to contemplate a range of values within the ordinary variability expected by one of ordinary skill in the art and suitable for the uses contemplated herein.

Among other things, disclosed herein are various embodiments of a surgical scaffold device that can be deployed in a laparoscopic procedure. Among other advantages, the scaffold helps mitigate some of the difficulties associated with certain laparoscopic procedures discussed above.

Figure 1A:
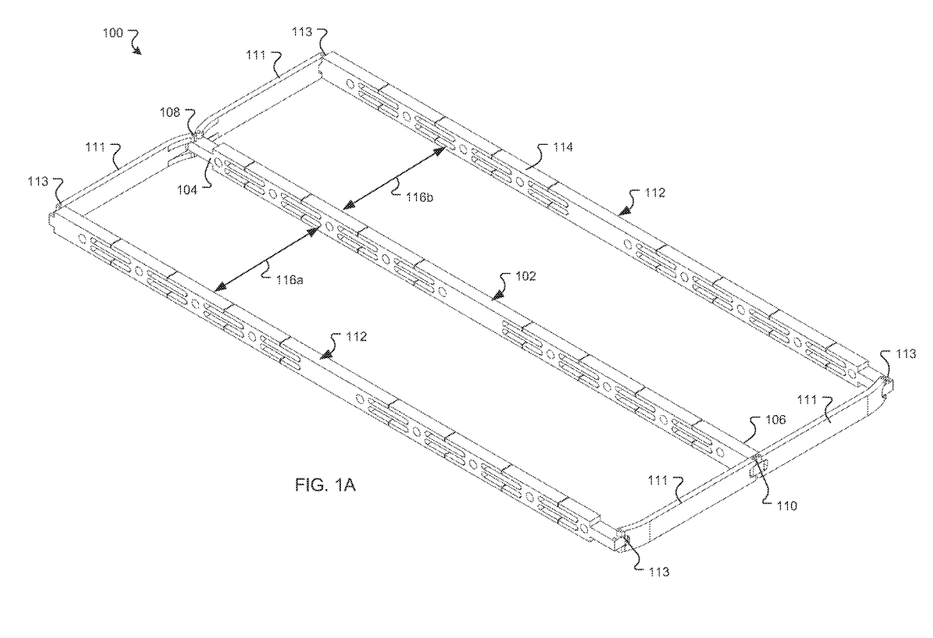
FIG. 1A is a perspective view of a surgical scaffold in a deployed state.

FIG. 1A is a perspective view of a surgical scaffold in a deployed state. The scaffold 100 may include a primary member 102 having a front end 104 and a back end 106. As used herein, the terms "front" and "back" are arbitrary terms employed for convenience only. These terms are not intended to convey any preferred orientation, function, or structure, or to suggest any intrinsic difference or similarity between the ends of the scaffold, or any other components referred to herein as "front" and "back" components. While certain differences may be noted below, these are provided only by way of exemplary embodiments and are not intended to limit the meaning of the terms "front" and "back" as described above. Similarly, terms such as "top" and "bottom" are provided for convenience only, and are not intended to convey any specific orientation, function, or structure unless explicitly noted to the contrary or otherwise clear from the context.

The primary member 102 may be coupled to lateral support members 111 by one or more front hinges 108 and back hinges 110. The hinges 108, 110 may, for example, be barrel hinges, pivot hinges, mortise hinges, flexural hinges, or any other type(s) of hinges suitable for use in a surgical device. The hinges 108, 110 may be integrally formed into the material of the primary member 102 and lateral support members 111 where these members meet, or the hinges 108, 110 may be separate mechanical components attached as appropriate to these members. In order for the scaffold 100 to deploy into a resilient working surface, the hinges 108, 110 may collectively articulate in a plane of articulation that contains the scaffold 100 (if the scaffold is not flexed, as described below). That is, the hinges 108, 110 may constrain motion of the connected elements so that they remain within a plane formed by the deployed scaffold 100, or stated alternatively, the hinges 108, 110 may rotate about an axis perpendicular to the plane formed by the deployed scaffold 100.

A lateral support member 111 may be rotatably coupled to the primary member 102 at each hinge 108, 110. Ancillary members 112 may be rotatably coupled to the lateral support member 111 by hinges 113. Although FIG. 1A shows two ancillary members 112, in principle any number of ancillary members may be employed. The terms "primary" and "ancillary" are terms of convenience only; there need not be any structural differences (or similarities) between primary and ancillary members, except in certain embodiments as noted below. The term "axial member" is used to collectively refer to either the primary or any ancillary member.

The primary member 102 and ancillary members 112 may include one or more flexural structures 114. The flexural structures 114 may be any structure(s) that allow a member to flex in a direction outside the plane of the scaffold. The flexural structures 114 may be advantageously constructed, e.g., as shown below, to facilitate planar deflection of the scaffold 100 while inhibiting in-plane movement (e.g., lateral displacement) of the individual axial members. Any suitable flexural structure 114 may be used, including but not limited to hinges, springs, or the like. Further details of some flexural elements suitable for use as the flexural structures 114 of the scaffold 100 are provided below.

The "deployed" state is characterized by the distances 116a, b between the primary member 102 and the ancillary members 112 being maximized, or more generally greater than a partially deployed or undeployed state.

Figure 1B:
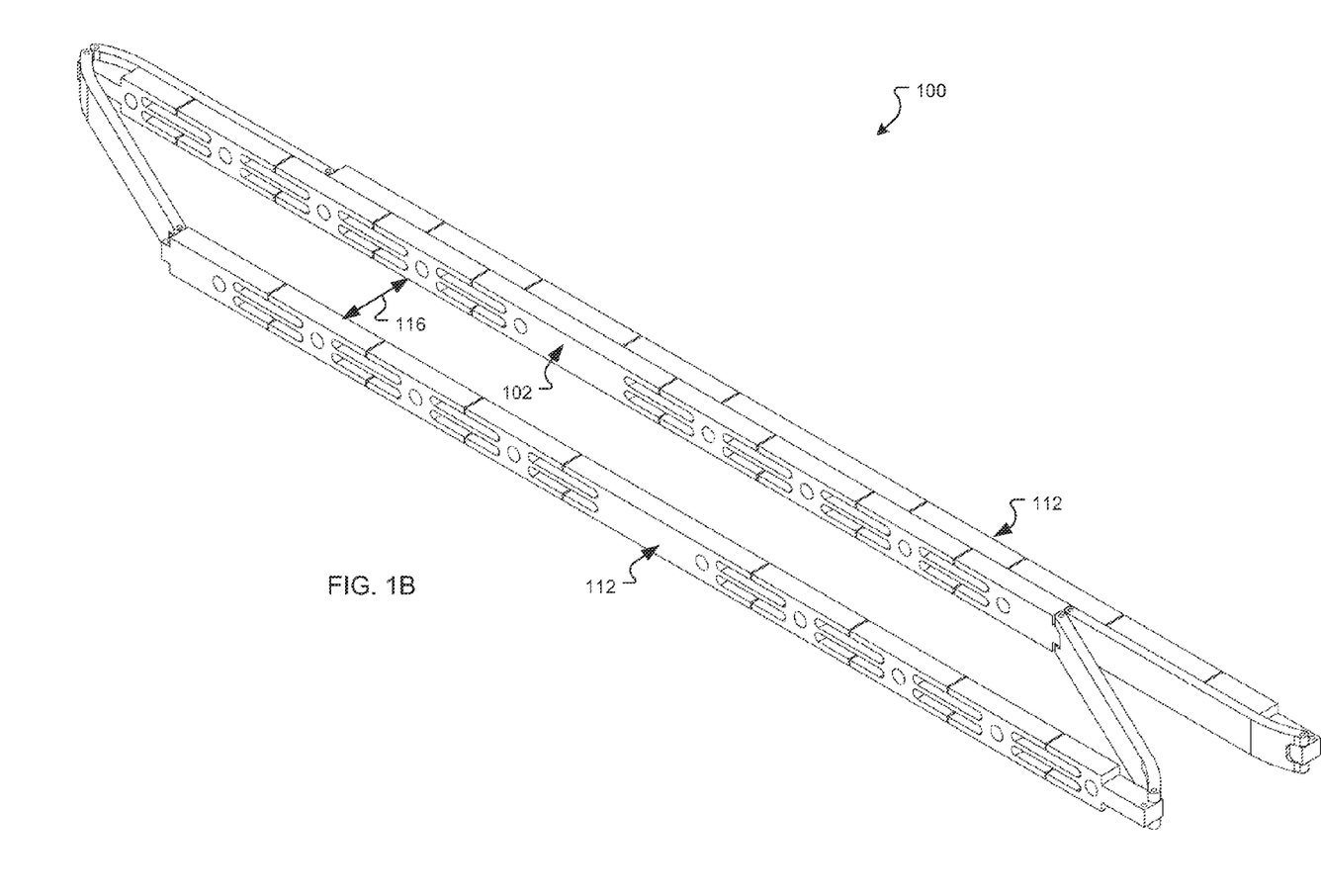
FIG. 1B is a perspective view of a surgical scaffold in a partially deployed state.
Figure 1C:
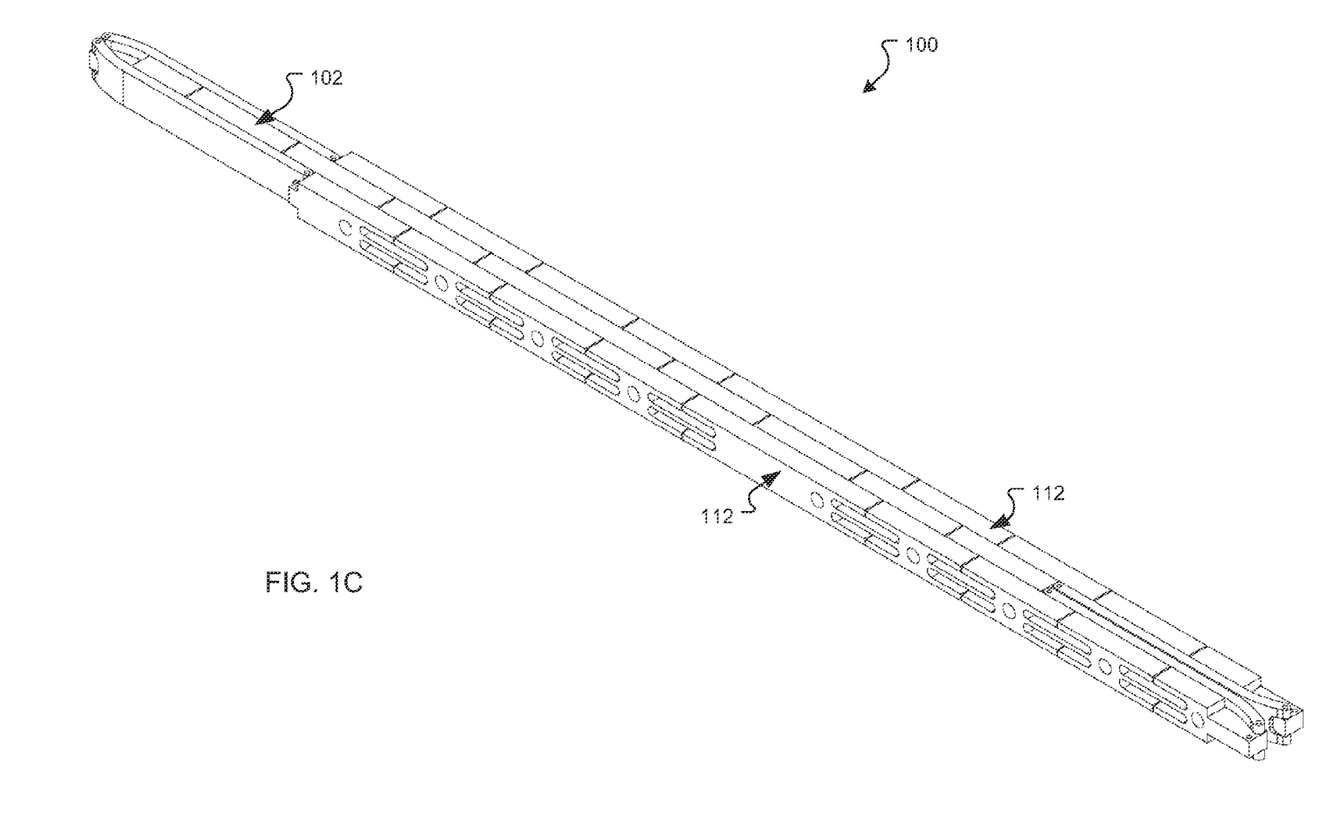
FIG. 1C is a perspective view of a surgical scaffold in an undeployed state.

FIG. 1B is a perspective view of the surgical scaffold in a partially deployed state. In general, the hinges described above facilitate a range of in-plane movements of the axial members of the scaffold 100 relative to one another between an undeployed state and a deployed state. A "partially deployed" state may be any relative position of the axial members characterized by at least one inter-member distance 116 between an ancillary member 112 and the primary member 102 being greater than in the undeployed state and less than in the deployed state. More specifically as depicted, one ancillary member 112 is fully collapsed and in contact with the primary member 102, while a second ancillary member 112 is partially collapsed FIG. 1C is a perspective view of the surgical scaffold in an undeployed state characterized by a minimized distance between the primary member 102 and the ancillary members 112. Although FIG. 1C shows an undeployed state with a minimized distance of zero—i.e., the members are in contact—in general this contact need not occur in an undeployed state.

In some uses, the scaffold 100 may be inserted into a patient's body through a trocar. Thus, in the undeployed state, the maximum cross-sectional distance across the scaffold 100 in a plane perpendicular to the axes of the members 102, 112 may be small enough to fit through such a trocar. Trocars in common use today may have inner diameters of approximately 10-15 mm, and the undeployed scaffold 100 may correspondingly have a cross section (perpendicular to the axis of the primary member 102) with a diameter of about 10-15 mm. In one aspect, the cross-sectional form of the ancillary members may be rounded or otherwise shaped to fit within a trocar barrel.

In some implementations, the length of scaffold 100 in the undeployed state may be long enough to fulfill the functions described herein, but not so long as to pose a safety risk to the patient during insertion through the trocar. In some implementations, the length of the scaffold 100 in its deployed state may be about eight inches, or between about seven inches and about ten inches. The ancillary members may be any suitable length, such as between about one inch and about two inches.

The scaffold 100 may be constructed of any material or combination of materials suitable for insertion into a living patient. This may include, for example, alloys such as surgical stainless steel, shape memory alloys, polymers, plastics, or the like. In one aspect, the scaffold 100 may be formed of relatively inexpensive materials such as a biocompatible polymer for use as a disposable surgical tool. In another aspect, the scaffold 100 may be formed of a surgical stainless steel or other autoclavable material suitable for repeated use.

Figure 2:
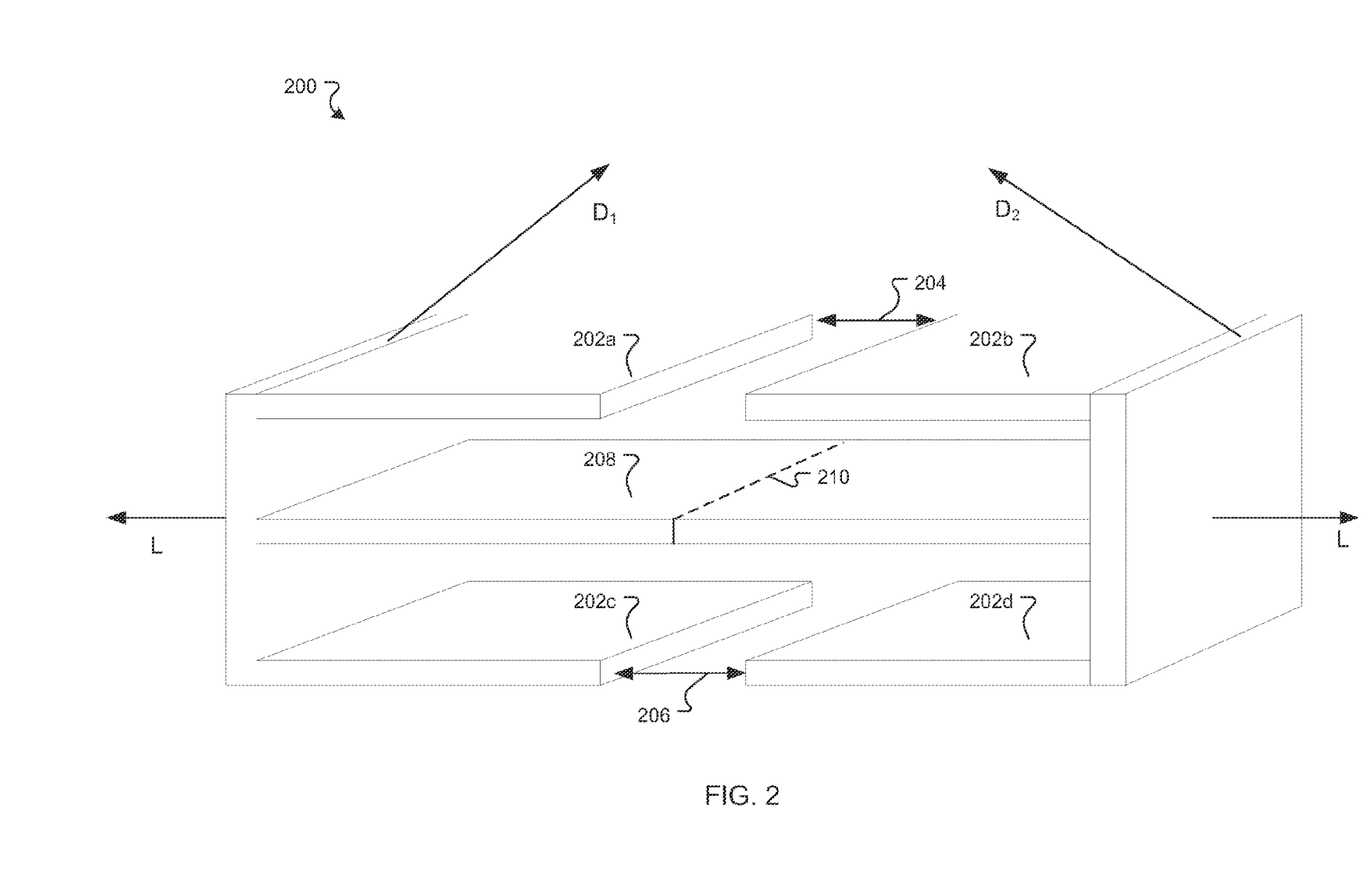
FIG. 2 is a schematic view of a flexural structure.

FIG. 2 is a schematic view of an exemplary flexural structure. The flexural structure 200 is shown relative to an axis L of the axial member that incorporates the flexural structure 200.

The flexural structure 200 may include axial protrusions 202a, b, c, d that extend axially toward one another without contacting one another when the flexural structure 200 is unflexed. The axial protrusions 202a, 202b may form a top layer that defines a top gap 204. Similarly, the axial protrusions 202c, 202d may form a bottom layer that defines a bottom gap 206. In general, the dimensions of the protrusions 202a, 202b, 202c, 202d (and therefore, the dimensions of the top and bottom gaps) need not be identical.

The flexural structure 200 may also include a middle layer 208. The middle layer may include a flexible region 210. Although shown schematically as a line in FIG. 2, the flexible region 210 may extend throughout the entire middle layer 208, or any subset thereof. The middle layer 208, and more generally, the flexible structure 200, may be formed from any resilient material suitable for insertion into a living patient, including the materials described above. In some implementations, the middle layer and/or flexible region may be relatively narrow, thereby providing sufficiently low stiffness to allow a desired degree of flexure. Similarly, the thickness of the middle layer 208 may depend upon the desired stiffness of the flexural structure 200, the material from which the flexural structure 200 and/or middle layer 208 are formed, and any other appropriate design constraints. For example, for a particular, predetermined stiffness, a substantially thicker middle layer 208 may be required if the middle layer 208 is formed from a medical grade polyurethane rather than surgical stainless steel.

When flexure-inducing forces are applied to the flexural structure 200, for example in the directions $D_1$ and $D_2$ shown in FIG. 2, the ends of the structure 200 will deflect, and the middle layer will flex, e.g. at the flexible region 210. As the flexural structure 200 continues to flex, one of the gaps 204 and 206 may shrink. For example, when the ends of the structure 200 move in the directions D1 and D2, the top gap 204 tends to close. If enough flex-inducing force is applied, then eventually an opposing pair of the protrusions 202a-d may come in contact, and the gap they define may disappear. In this state, the contact between the protrusions tends to inhibit any further flexure of the flexural structure 200. Thus, upward or downward flexural limits may be individually implemented at various points along the axial members by choosing the size of the top or bottom gaps 204, 206 at those points.

In some implementations, it may be desirable for the scaffold 100 to conform to the curved wall of a typical human's abdomen. As such, the flexural structures 200 may be shaped and sized to accommodate a corresponding deflection in the axial members of a scaffold. In some implementations, the axial members may be configured using the flexural structures 200 to permit an end-to-end deflection of some predetermined angle, such as five degrees or less, but to inhibit end-to-end deflection greater than the predetermined angle. It is within the ordinary skill in the art to determine shapes and sizes of the protrusions and gaps in each flexural structure 200 to accommodate this predetermined flexing behavior, and the variations and details are omitted here. In some implementations, an axial member may include flexural structures 200 and gaps/protrusions at predetermined intervals (e.g., at a pitch of one inch) or of a predetermined number to create a desired flexing behavior of the axial member(s).

Figure 3A:
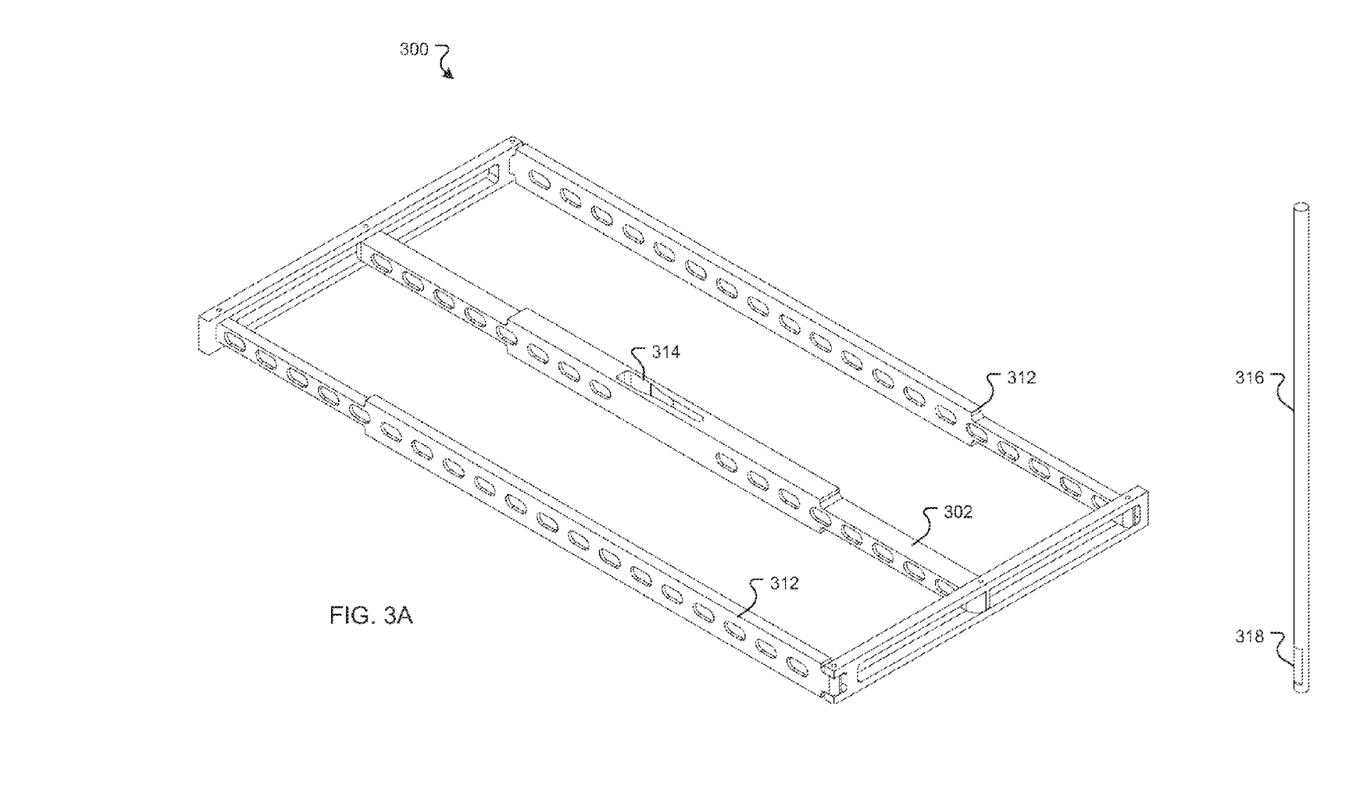
FIGS. 3A and 3B are a perspective view of a surgical scaffold with a retaining member.

FIG. 3A is a perspective view of a surgical scaffold with a retaining member. The scaffold 300 may include a primary member 302 and ancillary members 312 as described above. The scaffold 300 may also include a coupling 314 such as a through-hole with one or more coupling or registration features to removably and replaceably receive a retaining member 316 in a manner that facilitates manipulation of the scaffold 300 with the retaining member 316. Although the coupling 314 is shown in the primary member 302, in principle the coupling 314 can be located anywhere on the scaffold 300.

Figure 3B:
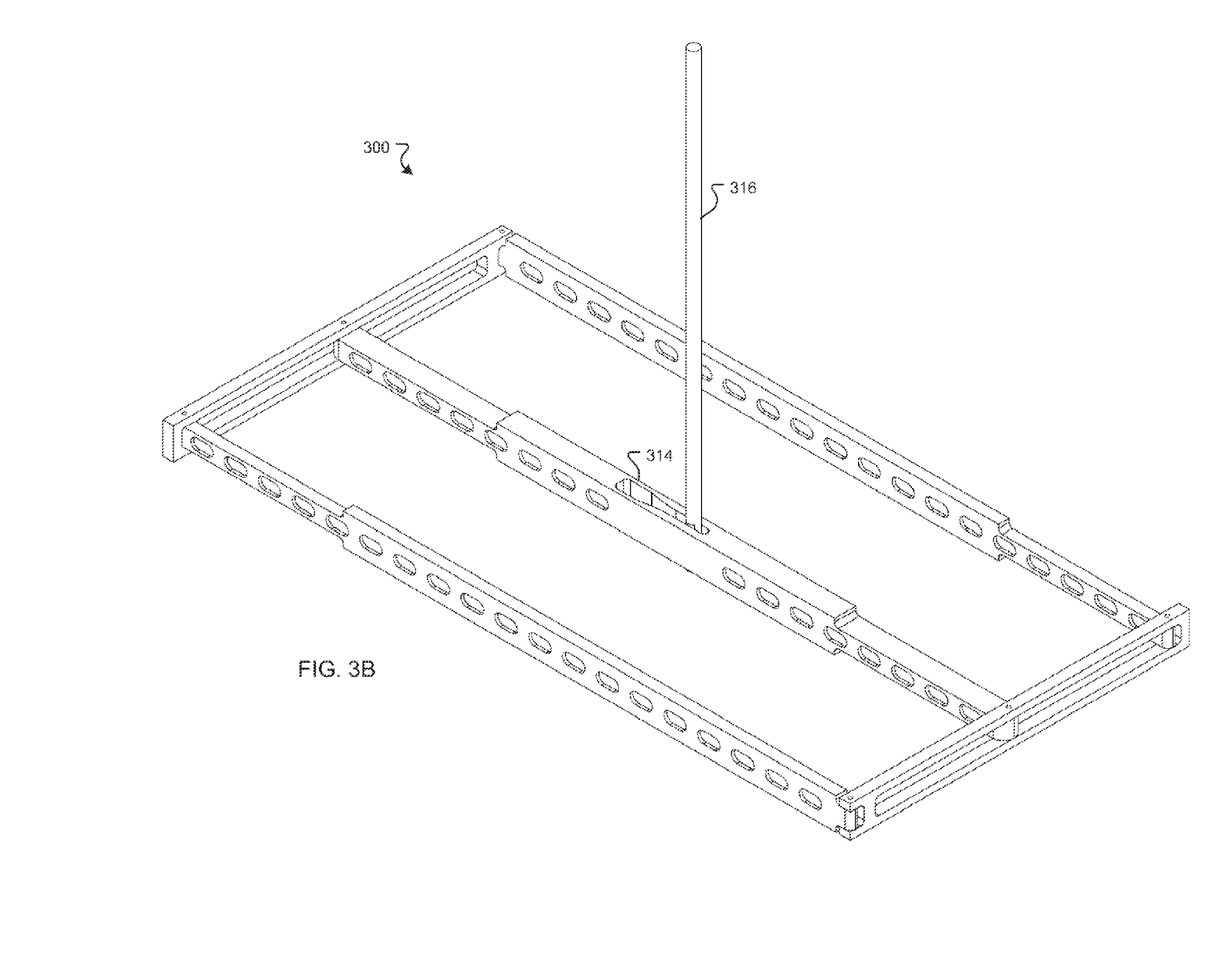

A separate retaining member 316 may also be provided. As described below, the retaining member 316 may be operable to help keep the scaffold 300 in place while the scaffold is deployed within a patient. The retaining member 316 may include a coupling 318 at its distal end that is configured to mate with the coupling 314 on the scaffold 300. FIG. 3B shows the retaining member 316 coupled to the scaffold 300 via the couplings 314 and 318 (not shown).

When the retaining member 316 is coupled to the scaffold 300, the couplings 314, 318 may be configured to allow the retaining member 316 to provide the scaffold with torque, a normal force, and an in-plane force in at least some directions. In this context, "normal" connotes the direction perpendicular to the plane of the scaffold, and "in-plane" connotes a direction parallel to the plane of the scaffold. In some implementations, applying force in certain in-plane directions is operable to disengage the retaining member 316 from the coupling 314, but force in other in-plane directions is operable to transfer such force to the scaffold 300. In some implementations, through a combination of applied normal and in-plane forces, the retaining member 316 may transfer a retaining force to the scaffold. "Retaining force" connotes force in a direction that is counter to the load on the scaffold 300 by an organ retained thereon. Thus, by application of a retaining force, the retaining member 316, may permit a surgeon to lift or otherwise retract an organ from a surgical site within an abdominal cavity.

The retaining member 316 may be inserted through the patient's abdominal cavity to engage the scaffold 300 once the scaffold has been deployed within the cavity. In some implementations, the retaining member 316 has a cross-sectional area small enough to minimize scarring in the resultant puncture. In some implementations, the retaining member 316 may have maximum cross sectional distance less than two millimeters.

In some implementations, the couplings 314, 316 may also include an electrical coupling. The electrical coupling may be operable to provide power or control signals from an external source to additional elements on the scaffold 300, as described more fully below. In some implementations, one or more electrical couplings can be located elsewhere on the scaffold 300. In some implementations, the electrical couplings can receive power or control signals through one or more wires fed through the insertion trocar.

Figure 4:
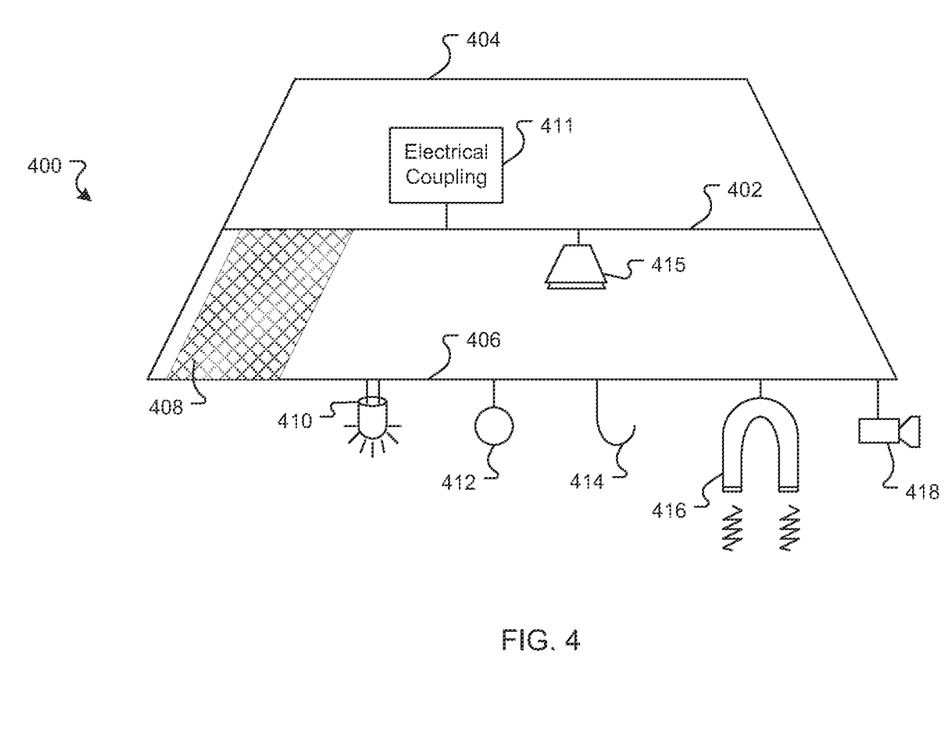
FIG. 4 is a schematic view of a surgical scaffold with additional elements.

FIG. 4 is a schematic view of a surgical scaffold with additional elements. The additional elements described below may be useful during some laparoscopic procedures.

The scaffold 400 may have a short ancillary member 404 and a long ancillary member 406 so that the scaffold deploys in the shape of a trapezoid. This may be advantageous when an anticipated use of the scaffold 400 involves positioning it with one end (e.g., the short end) in a relatively small space, such as abutting the patient's diaphragm. More generally, the scaffold 400 can include ancillary members having different dimensions that result in any other perimeter geometry that conforms to an anticipated deployment site.

The scaffold 400 may include a mesh 408 deployed between two members. The mesh 408 may advantageously help retain some of the patient's anatomical structures in a safe location during the surgical procedure. The mesh 408 may be constructed from any suitable biocompatible material, including polymer threads such as nylon or polyester, natural threads such as silk, or the like. Although the mesh 408 is shown in only a portion between the members 402 and 406, in principal the mesh 408 can extend throughout the entire space between any two members, or any portion thereof.

The scaffold 400 may include one or more light sources 410, including but not limited to light emitting diodes (LEDs). The light source 410 may provide illumination to the surgical site. Moreover, using more than one light source 410 may mitigate the effect of shadows and reduce the chances of obstructing illumination with the movement of surgical instruments. As such, the scaffold 400 may include two light sources, three light sources, or any other number of light sources suitable for illuminating surfaces of interest in a surgical procedure. In some implementations, the light sources 410 may be provided with power and/or control signals from an external source via the retaining member through an electrical coupling 411.

The scaffold 400 may include one or more loops 412. The loops 412 may advantageously serve as tie points that can be used to anchor organs or other surgical tools to the scaffold 400 using surgical thread, clamps, or the like. Similarly, the scaffold 400 may include one or more hooks 414 or clamps 415 that may be similarly employed to secure tissue or surgical instruments as appropriate.

The scaffold 400 may include a high-friction surface (e.g., the top side or a portion thereof), such as a textured or knurled surface, that may help promote organ retention. The top side of the scaffold 400 may also or instead include one or more regions having a relatively soft or pliable coating to mitigate irritation to the patient's abdominal wall or diaphragm from the scaffold 400. The pliable coating may include any soft surgical material, such as rubber, silicone, other elastomers, or the like.

The scaffold 400 may include one or more magnets 416. The magnets 416 may include permanent magnets or electromagnets. In embodiments involving electromagnets, the electromagnets 416 may receive power and/or control signals from an external source via the retaining member through an electrical coupling 411. The magnets 416 may advantageously provide locations to easily and securely place magnetic surgical tools or other magnetic materials.

The scaffold 400 may include one or more video cameras 418. The video camera(s) 418 may receive power and/or control signals from an external source via the retaining member through an electrical coupling 411. The video camera(s) 418 may also send a video signal to an outside receiver through the electrical coupling, or the video camera(s) 418 may transmit video wirelessly using, e.g., radio frequency communications. The video camera(s) 418 may be movably connected to the scaffold 400, such as by removably and replaceably coupling a video camera 418 to the scaffold 400, or by including a universal joint or the like in a mechanical coupling from the video camera 418 to the scaffold 400. In this manner, the field of view of one of the video cameras 418 may be adjusted during the surgical procedure. In some implementations, two or more cameras 418 may be mounted on the scaffold 400 such that every camera has a field of view that overlaps with the field of view of at least one other camera.

Figure 5:
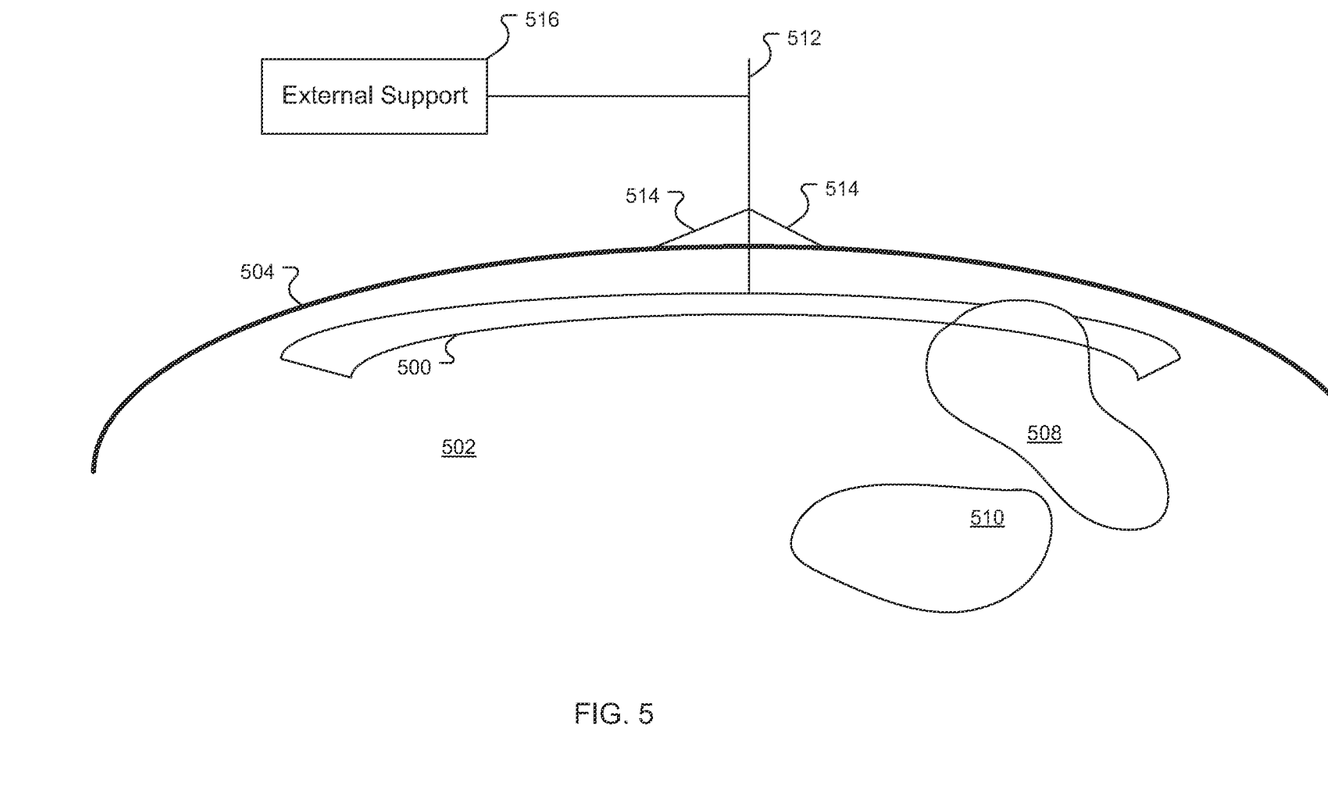
FIG. 5 is a schematic view of a surgical scaffold deployed during a surgical procedure.

FIG. 5 is an exemplary schematic cross-sectional view of a surgical scaffold deployed in a human patent during a surgical procedure. In this example, the scaffold 500 is deployed within the abdominal cavity 502 defined in part by the patient's abdominal wall 504. An obstructing organ 508 (e.g., the liver) is secured to the platform 500 by any of the techniques described above, thus exposing the surgical target 510 (e.g., the gallbladder). Thus, a surgeon may access the surgical target 510. Moreover, the overhead clearance of the surgical target 510 is relatively well utilized, inasmuch as the scaffold 500 substantially conforms to the patient's abdominal wall 504. Although FIG. 5 shows a gap between the scaffold 500 and the abdominal wall 504, this has been shown for clarity. The scaffold 500 may contact the abdominal wall 504 to a substantial degree, such as where the scaffold 500 is also used to lift the abdominal wall 504 away from the surgical site.

The scaffold 500 is held in place by a retaining member 512. In some implementations, the retaining member 512 may be further stabilized with support structures 514 that mechanically couple the retaining member to the patient. In some implementations, the retaining member 512 may be further stabilized via a mechanical coupling to an external support 516. The external support 516 may include any manner of structures—e.g., clamps, graspers, vices, magnets, actuators, etc.—that may be collectively operable to hold the retaining member 512 in a fixed or otherwise controllable position.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A device comprising:
   a primary member having:
      a front end and a back end;
      a front hinge and a back hinge, that collectively articulate in a plane of articulation;
   an ancillary member movably connected to the primary member via the front hinge and the back hinge; wherein
   the primary member and ancillary member are:
      constructed from a surgical material; and
      individually flexible in a direction perpendicular to the plane of articulation to a degree substantially conforming to a human abdomen; and further wherein
   the device is configured to transition between a first state and a second state by articulating the hinges, in which the first state is characterized by minimizing a distance between the primary member and the ancillary member and the second state is characterized by maximizing the distance between the primary member and the ancillary member, in which a maximum device cross section in the first state is suitable for insertion through a trocar in a laparoscopic procedure on a human; and
   a number of independent flexural structures in each of the primary member and ancillary member to facilitate flexure in the direction perpendicular to the plane of articulation, each independent flexural structure including an opposing pair of axial protrusions extending toward one another across a gap within the plane of articulation when the flexural structure is unflexed, wherein the opposing pair of axial protrusions impose a flexural limit at a point where a deflection of a corresponding one of the independent flexural structures causes the opposing pair of axial protrusions to come in contact across the gap.

2. The device of claim 1, wherein each one of the flexural structures includes a top layer, a flexible middle layer, and a bottom layer, in which the top and bottom layers each include a plurality of gaps that facilitate a deflection of the flexible middle layer and inhibit the deflection beyond an upward and a downward flexural limit according to a size of one or more corresponding top or bottom ones of the plurality of gaps.

3. The device of claim 1, further including an electrical coupling site.

4. The device of claim 3, further comprising a light source electrically coupled to the electrical coupling.

5. The device of claim 4, wherein the light source is movably coupled to at least one of the primary member and the ancillary member.

6. The device of claim 3, further comprising a camera electrically coupled to the electrical coupling site.

7. The device of claim 6, wherein the camera is movably coupled to at least one of the primary member and the ancillary member.

8. The device of claim 6, further comprising a plurality of cameras, each camera having a corresponding field of view, wherein the field of view of any camera in the plurality overlaps with at least one other field of view of at least one other camera in the plurality.

9. The device of claim 1, further comprising an attachment point for anchoring an organ.

10. The device of claim 9, wherein the attachment point is selected from the group consisting of: a textured surface, a hook, a clamp, a loop, and a magnet.

11. The device of claim 10, wherein a perimeter of the device bears a trapezoidal geometry when the device is in the second state.

12. The device of claim 1, further comprising a pliable mesh between the primary and ancillary members.

13. The device of claim 1, wherein the articulating hinges include a shape memory alloy.

14. The device of claim 1, wherein a top side of the device is constructed from a soft material.

15. The device of claim 1, further comprising a second ancillary member coupled to the primary member.

16. The device of claim 1, wherein the primary member further has a first coupling configured to mechanically couple to a retaining member not in the plane of articulation.

17. The device of claim 16, wherein the first coupling is dimensioned to mechanically couple to a retaining member of cross sectional area less than four square millimeters.

18. The device of claim 16, wherein the first coupling is configured to transfer torque, normal force, and in-plane force in at least one direction from the retaining member to the device.

19. A device comprising:
   a primary member having:
      a front end and a back end;
      a front hinge, a back hinge, that collectively articulate in a plane of articulation;
   an ancillary member movably connected to the primary member via the front hinge and the back hinge; wherein
   the primary member and ancillary member are:
      constructed from a surgical material; and
      individually flexible in a direction perpendicular to the plane of articulation and configured to inhibit deflection greater than five degrees; and further wherein
   the device is configured to transition between a first state and a second state by articulating the hinges, in which the first state is characterized by minimizing a distance between the primary member and the ancillary member and the second state is characterized by maximizing the distance between the primary member and the ancillary members, in which a maximum device cross section in the first state is suitable for insertion through a trocar in a laparoscopic procedure on a human; and a number of independent flexural structures in each of the primary member and ancillary member to facilitate flexure in the direction perpendicular to the plane of articulation, each independent flexural structure including an opposing pair of axial protrusions extending toward one another across a gap within the plane of articulation when the flexural structure is unflexed, wherein the opposing pair of axial protrusions impose a flexural limit at a point where a deflection of a corresponding one of the independent flexural structures causes the opposing pair of axial protrusions to come in contact across the gap.

20. The device of claim 19, wherein the device further includes a first coupling configured to mechanically couple to a retaining member not in the plane of articulation.

21. An expandable structure having an expanded state forming a plane shaped and sized to support an organ during a minimally-invasive surgical procedure and a collapsed state shaped and sized to fit through a trocar for delivery to a surgical site for the minimally-invasive surgical procedure, the expandable structure comprising:

two or more axial members, each individually flexible in a direction perpendicular to the plane to conform to an abdominal cavity;

two or more lateral support members;

a number of hinges coupling the two or more lateral support members to the two or more axial members to facilitate a movement of the axial members and lateral support members within the plane between the expanded state and the collapsed state; and a number of independent flexural structures in each of the two or more axial members to facilitate flexure in the direction perpendicular to the plane, each independent flexural structure including an opposing pair of axial protrusions extending toward one another across a gap within the plane when the flexural structure is unflexed, wherein the opposing pair of axial protrusions impose a flexural limit at a point where a deflection of a corresponding one of the independent flexural structures causes the opposing pair of axial protrusions to come in contact across the gap.

* * * * *